(12) United States Patent
Bell (10) Patent No.: US 11,139,053 B2
(45) Date of Patent: Oct. 5, 2021

(54) PATIENT SERVICES DESKTOP

(71) Applicants: KNO2 LLC, Boise, ID (US); Therasa Bell, Boise, ID (US)

(72) Inventor: Therasa Bell, Boise, ID (US)

(73) Assignee: KNO2 LLC, Boise, ID (US)

( * ) Notice: Subject to any disclaimer, the term of this patent is extended or adjusted under 35 U.S.C. 154(b) by 60 days.

(21) Appl. No.: 16/099,302

(22) PCT Filed: May 5, 2017

(86) PCT No.: PCT/US2017/031295
§ 371 (c)(1),
(2) Date: Nov. 6, 2018

(87) PCT Pub. No.: WO2017/192989
PCT Pub. Date: Nov. 9, 2017

(65) Prior Publication Data
US 2019/0214115 A1 Jul. 11, 2019

Related U.S. Application Data

(60) Provisional application No. 62/333,020, filed on May 6, 2016, provisional application No. 62/413,308, filed
(Continued)

(51) Int. Cl.
*G16H 10/60* (2018.01)
*G16H 40/67* (2018.01)
(Continued)

(52) U.S. Cl.
CPC ............. *G16H 10/60* (2018.01); *G16H 40/40* (2018.01); *G16H 40/67* (2018.01); *G16H 80/00* (2018.01)

(58) Field of Classification Search
CPC .............................. G16H 10/60; G16H 80/00
See application file for complete search history.

(56) References Cited

U.S. PATENT DOCUMENTS 7,620,658 B2 * 11/2009 Benson ............. H04L 29/12169
8,621,025 B2 * 12/2013 Ridgard ............. H04L 67/1095
709/207

(Continued)

*Primary Examiner* — Michael Tomaszewski
*Assistant Examiner* — Jay M. Patel
(74) *Attorney, Agent, or Firm* — Finnegan, Henderson, Farabow, Garrett & Dunner, LLP (57) ABSTRACT

A process for configuring an account for a desktop application uses a central data processing facility to configure a release for a trading partner, which release includes the preferred method of receiving documents and preferred format for the content; configures an intake download by storing settings for how to export and import documents; configures intake rules to determine how to route received documents; installs a Desktop from the web portal onto a local data processing system; and automatically synchronizing the Desktop to the portal. A process for ensuring the secure delivery of information about a patient sends a verification fax sheet to a fax number of a recipient instructing the recipient to go to a website; validates the recipient after the recipient has visited the website; tests the recipient at the website using questions specific to the patient; and sends the confidential information to the fax number if the recipient passes the test.

14 Claims, 13 Drawing Sheets

Related U.S. Application Data on Oct. 26, 2016, provisional application No. 62/414,632, filed on Oct. 28, 2016.

(51) Int. Cl.
*G16H 80/00* (2018.01)
*G16H 40/40* (2018.01)

(56) References Cited

U.S. PATENT DOCUMENTS

| | | | |
|---|---|---|---|
| 2010/0306858 A1* | 12/2010 | McLaren | G06F 19/00 726/28 |
| 2011/0047230 A1* | 2/2011 | McGee | H04L 41/12 709/206 |
| 2014/0237626 A1* | 8/2014 | Marcus | G06F 21/10 726/28 |
| 2014/0372965 A1* | 12/2014 | Alibakhsh | G16H 20/30 717/101 |
| 2015/0222625 A1* | 8/2015 | Ford | H04L 65/403 726/7 |
| 2016/0063209 A1* | 3/2016 | Malaviya | G16H 50/30 706/12 |
| 2016/0070924 A1* | 3/2016 | Saliba | G16H 10/60 705/3 |
| 2016/0210413 A1* | 7/2016 | Janjua | G16H 30/20 |

\* cited by examiner

Direct_Discharge

Direct_Dr Elwell

Direct_Dr Schoch

Direct_Dr. Collins

Direct_Dr. Jones Office

Direct_Release Information

Direct_Results

Dr Smith

Dr. Bob Smith

Important! Do not include any patient or personally identifiable information

Release Name: Direct_Dr Elwell

Origin Address or Fax Number: drmiller@caringhandsvillage.direct.kn...x

Destination Address or Fax Number: elwellmd@greenway.direct.com

Default Send Type: ○ Original  ○ PDF  ⦿ CDA

Cancel   Save Changes drjonescaringhandsvillage.direct.kno2fy-integration.com bobsmith@gree...

FIG. 3B

| Releases ^ | Origin Address or Fax Number | Destination Address or Fax Number | | |
|---|---|---|---|---|
| Direct_Discharge | discharge@caringhandsvillage.direct.kno2fy-integration | alerts@hopefulhomecare.direct.kno2fy-integration.com | / | ✕ |
| Direct_Dr Elwell | drmiller@caringhandsvillage.direct.kno2fy-integration | elwellmd@greenway.direct.com | / | ✕ |
| Direct_Dr Schoch | alerts@caringhandsvillage.direct.kno2fy-integration | scoch@athenahealth.direct.com | / | ✕ |
| Direct_Dr. Collin | alerts@caringhandsvillage.direct.kno2fy-integration | collin@allscripts.direct.com | / | ✕ |
| Direct_Dr. Jones Office | records@caringhandsvillage.direct.kno2fy-integration | alerts@hopefulhomecare.direct.kno2fy-integration.com | / | ✕ |
| Direct_Release of Information | records@caringhandsvillage.direct.kno2fy-integration | alerts@hopefulhomecare.direct.kno2fy-integration.com | / | ✕ |
| Direct_Results | results@caringhandsvillage.direct.kno2fy-integration | results@caringhandsvillage.direct.kno2fy-integration.com | / | ✕ |
| Dr. Smith | drjones@caringhandsvillage.direct.kno2fy-integration | drsmith@athenahealth.direct.com | / | ✕ |
| Dr. Bob Smith | drjones@caringhandsvillage.direct.kno2fy-integration | bobsmith@greenway.direct.com | / | ✕ |
| Fax Document | 208-576-7623 | 208-576-7620 | / | ✕ |

Documents > Kno2Release

| Name | Date modified | Type |
|---|---|---|
| QuickSend | 4/26/2017 2:46 PM | File folder |
| Direct_Dr Elwell | 3/22/2017 12:11 PM | File folder |
| Direct_Dr. Schoch | 3/22/2017 10:21 AM | File folder |
| Direct_Dr. Collin | 3/22/2017 10:21 AM | File folder |
| Direct_Dr. Jones Office | 3/22/2017 10:21 AM | File folder |
| Direct_Release of Information | 3/22/2017 10:21 AM | File folder |
| Direct_Results | 3/22/2017 12:29 PM | File folder |
| Dr Smith | 3/22/2017 10:21 AM | File folder |
| Dr. Bob Smith | 3/22/2017 10:21 AM | File folder |
| Fax Document | 3/22/2017 10:21 AM | File folder |
| Referral 2 | 3/22/2017 10:21 AM | File folder |

PATIENT SERVICES DESKTOP

A. FIELD OF THE INVENTION

This invention relates generally to systems and methods to enhance ease and security for document transfer and, more particularly, to computerized systems and methods for exchanging healthcare documents efficiently and securely.

BACKGROUND

Professionals in health-care systems create and exchange an unwieldy amount of files, records, and documents for individual patients every day. By some estimates, primary care (PCPs) physicians frequently share information with an average of 60 other providers. To ensure quality care for patients who may require services from more than one organization, each organization may need access to the documents and data produced and stored by another organization.

Despite the technology advances in healthcare, facsimile transmission (fax) continues to the dominant method for exchanging patient information. Fax, unfortunately is not a very secure way to exchange information. For example, fax numbers may be miskeyed or the person sending the message may inadvertently select the wrong fax number, such as one for a provider not involved in the care of the patient to whom the information relates.

Even without a mistake, the party sending the information may retrieve a number that is no longer valid or owned by the intended recipient. And even if the number is correct, many things can happen if the intended recipient is not actively managing the fax machine or server. For example, the patient information may not be readily accessible to the intended recipient, or inappropriate individuals may see the information if they are at the unattended machine when faxed documents arrive.

Some health systems and hospitals manage this risk manually. For example, they call organizations or providers on a scheduled basis to verify the accuracy and currency of their fax numbers. This is slow and expensive.

Other healthcare providers ignore the risk and seek to solve the problems with a cover sheet on the fax that directs the recipient to notify the sender and discard the fax if received by the wrong person. There is no way to ascertain if the recipients do this.

With the rise of the Internet, many organizations exchange clinical documents online, using equally unsecure technologies, such as email. This practice also threatens the confidentiality of patient information.

As patient and legislative awareness of the importance of patient privacy has increased, however, so has the need for ways to exchange clinical documents securely and conveniently.

B. SUMMARY OF THE INVENTION

A Desktop consistent with the invention provides great functionality very efficiently. It automates the transmission of messages (documents) using a variety of channels, and fits smoothly into the workflows of healthcare organizations. For example, the Desktop allows a user to send patient information from an EMR or other patient-charting system without having to leave a current workflow. Pop-up notifications alert users to received messages without forcing the user to log in to a portal.

In particular, in a system for exchanging information coupled to a web portal, a process for configuring an account for a desktop application consistent with the invention comprises the steps of: configuring a release for a trading partner by a central data processing facility, including a preferred method of receiving documents and a preferred format for the content; configuring an intake download by the central data processing facility by storing settings for exporting documents from the system and imported and importing documents into the system; configuring intake rules by the central data processing facility to determine how to route received documents; and installing a Desktop from the web portal onto a local data processing system, and automatically synchronizing the Desktop to the portal.

Another process consistent with the invention for sending a message from a Desktop on a local data processing system in a system for exchanging information coupled to a web portal includes the steps of searching, from the Desktop, a database for information about the subject of the message; selecting, from the Desktop, a document to accompany the message; sending, from the Desktop, the document to a quick-release-type folder for the intended recipient; preparing a message and sending a notification, from the Desktop, to the intended recipient about the message; automatically populating fields in the message with any known information from the portal; and sending the message from the Desktop.

Another process consistent with the invention for ensuring the secure delivery of information about a patient in a system for transmitting confidential information comprises the steps of sending, from a local machine, a verification fax sheet to a fax number of a recipient instructing the recipient to go to a website; validating the recipient after the recipient has visited the website; testing the recipient at the website using questions specific to the patient; and sending the confidential information to the fax number if the recipient passes the test.

C. BRIEF DESCRIPTION OF DRAWINGS

The accompanying drawings, which are incorporated in and constitute a part of this disclosure, illustrate several embodiments and aspects of this disclosure, and together with the description, explain certain principles of the invention.

FIG. 4A is a diagram showing web release settings synchronized to a local directory and subdirectories

D. DETAILED DESCRIPTION

The Kno2system is a patient-document-exchange platform that supports many types of content/information and common methods of exchange. Accessing the system can occur through APIs, a web portal, and now, through a Desktop.

The Desktop is a lightweight, installed client that uses locally managed directories and fileshares to automate the exchange of patient information. The Desktop allows a healthcare provider to capture and exchange patient records from multiple sources, and send them as a consolidated message to another provider without having to log into a web portal.

Embodiments consistent with the invention include systems, methods, and computer-readable media for exchanging data between users, such as organizations that provide medical care for patients. Data may include messages, notes, images, clinical documents, and any other data relevant to patient care.

Data exchange may occur according to protocols to ensure protection of patient privacy. A protocol may include requirements for identity verification, such as compliance with one of the ID proofing levels of the National Institute of Standards and Technology. A protocol may further include a standard or set of standards for secure communication, such as asymmetric cryptography, registration with a central database authority, or a certain level of security from point to point, e.g., from sender to receiver.

Figure 1:
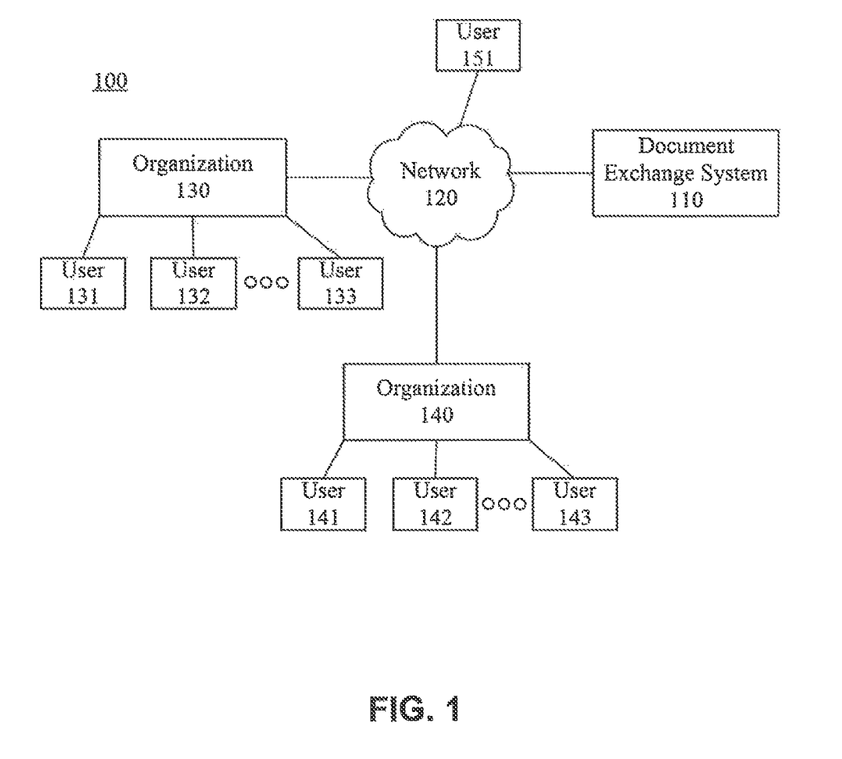
FIG. 1 shows an exemplary system environment for implementing embodiments consistent with the invention.

FIG. 1 illustrates an exemplary system environment 100 for clinical document-exchange, but the invention is not limited to that environment, and may handle other forms of electronic communications, such as insurance documents or legal communications. The arrangement and number of components in FIG. 1 are exemplary only.

System environment 100 includes document-exchange system 110, network 120, organizations 130 and 140, and users 131, 132, 133, 141, 142, 143, and 151. Document-exchange system 110 may include components of the system described further below in reference to FIG. 2. Organizations 130 and 140, such as hospitals or clinics, interact with document-exchange system 110. Each organization may include users (e.g., doctors or staff) the actually interact with document-exchange system 110.

Figure 2:
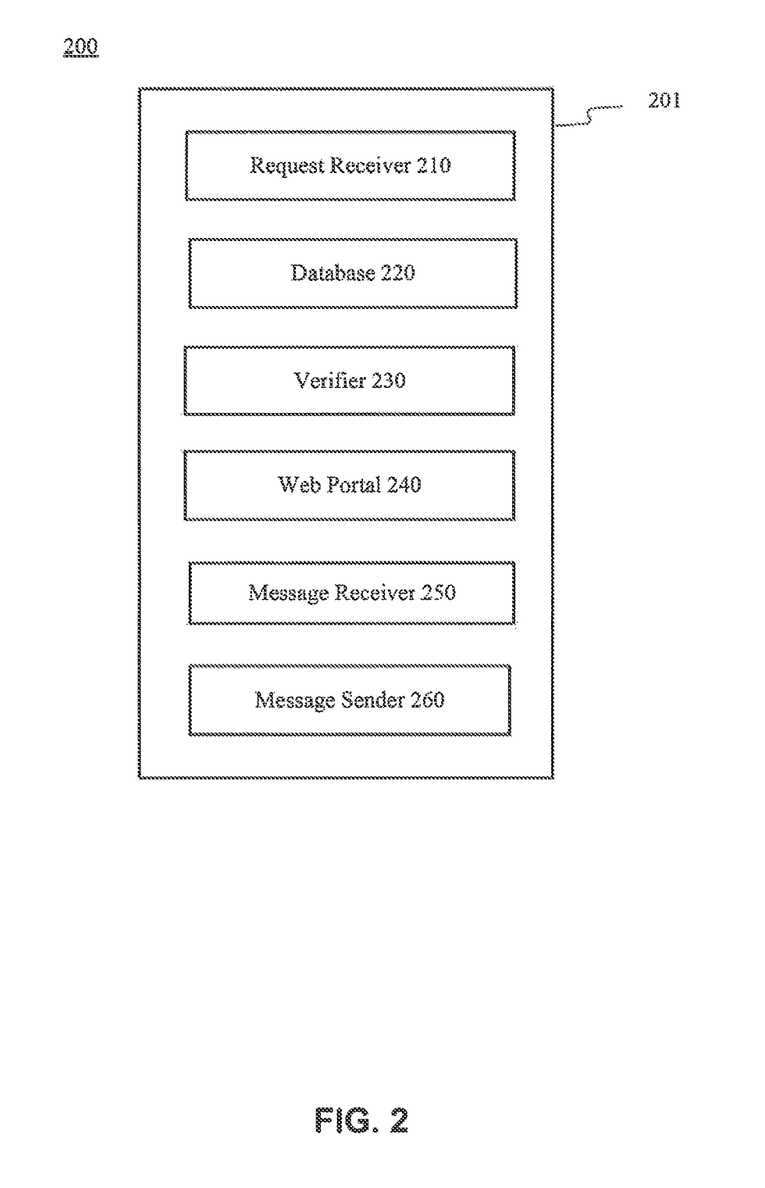
FIG. 2 shows the exemplary system in FIG. 1 in more detail.

FIG. 2 illustrates an exemplary system 200 for implementing embodiments consistent with this invention. System 200 includes document-exchange system 201, which includes request receiver 210, database 220, verifier 230, web portal 240, message receiver 250, and message sender 260. These components of system 200 may be implemented using any suitable combination of hardware, software, and firmware. The components may correspond to functional blocks implemented with a set of instructions executed by suitable hardware (e.g., a computer, a server, a group of computers, or one or more computing nodes operating over a network). The components may also correspond to programmable, fixed-function hardware, such as programmable-logic devices, such as PALs, PLAs, CPLDs, or FPGAs. The number and arrangement of components in FIG. 2 is merely provided for illustration.

Request receiver 210 may receive registration requests from organizations. For example, organization 130 may send requests through document-exchange system 201. Registration requests may also originate from users, which can also indicate their association with one or more organizations.

Request receiver 210 may access database 220, for example to determine whether the requesting user or organization already has access to document-exchange system 201. Request receiver 210 may then send the registration request along with any supplied data to verifier 230.

Database 220 may store data used by document-exchange system 201. Database 220 may store user and organizational information, such as to indicate an organization has registered with document-exchange system 201 or has been provisioned a sub-domain. Database 220 may also store information to indicate a user has registered with the document-exchange system or has been provisioned a user address. Database 220 may also store data describing the relationship between users and organizations. Database 220 may also store other information associated with the operation of document-exchange system 201, such as organizational sub-domains or message templates from document-exchange system 201. In short, database 220 may store any information related to the operation of document-exchange system 201 and the foregoing examples are provided by way of example and are by no means exhaustive.

Verifier 230 may verify registration requests from users and organizations. Verifier 230 may also verify the identity of the requesting representative of the organization and the organization's name and address. Other examples of verification are set forth below.

Web portal 240 may provision organizational sub-domains, but only provision an organizational sub-domain after verifier 230 has successfully verified a registration request from an organization. Web portal 240 may store an organizational sub-domain in database 220. Web portal 240 could create a virtual representation of an organization in the form of a sub-domain that is part of a larger domain and store the representation in database 220. For example, web portal 240 may create a directory structure corresponding to the organizational sub-domain in database 220.

Web portal 240 may allow access to the organizational sub-domain through an interface, such as a web page. Web portal 240 may also allow access to an organizational sub-domain through another interface, such as a dedicated software platform used an organization and provide access to the sub-domain through that platform.

Web portal 240 may allow an organization's representative to interact with its sub-domain. Web portal 240 could provide the organization with a login to access the organization's sub-domain. For example, web portal 240 may provide a login that allows a representative of the organization to add and remove authorized users to the organization's sub-domain. Web portal 240 may also allow an organization's representative to interact with its sub-domain through other means. For example, web portal 240 may detect the computer from which a representative attempts to access the sub-domain through its IP address and save information about the computer to database 220. Web portal 240 may use or combine other security measures, such as requiring a signed digital certificate before allowing an organization's representative to interact with the sub-domain.

Web portal 240 may also allow an organization's representative to enter information about the organization, its users, and its organizational structure. Such information may include information relating to the hierarchical structure of the organization, such as its subdivision into departments, information relating to the physical location of individuals in the organization, such as geographic location, or physical location in a building or floor, or relational information in a conceptual subgroup.

Software for the desktop resides on the computers for users 131-133, 141-143, and 151, and is downloadable from the web portal 240. Updates, new releases, and bug fixes come also through the portal.

Figure 3A:
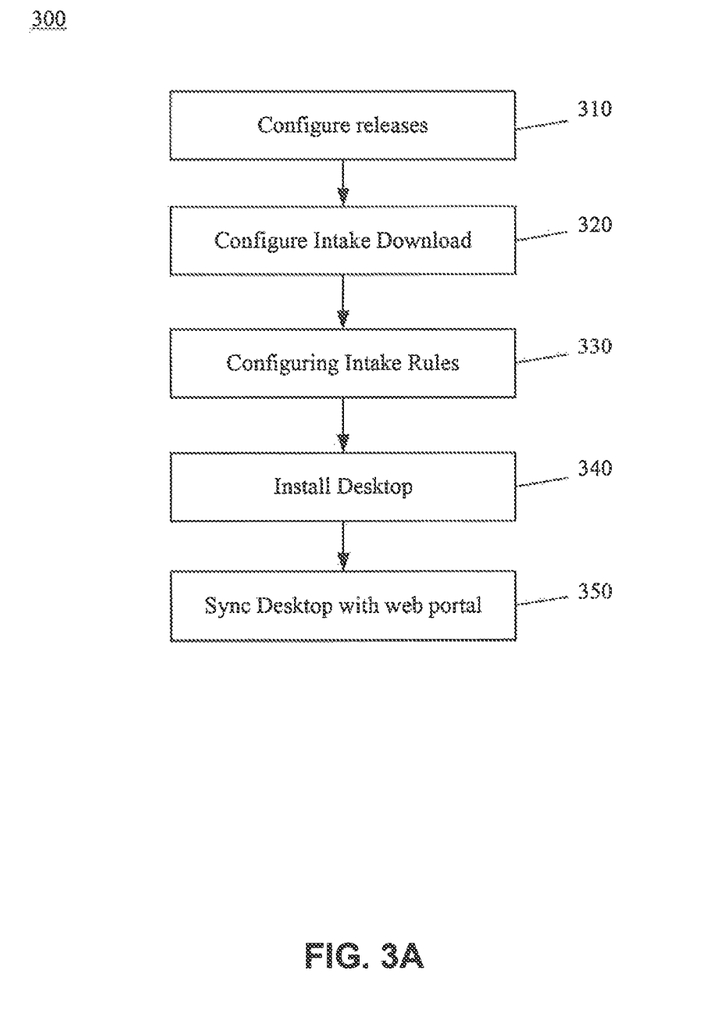
FIG. 3A shows a flowchart for configuring the Desktop.

Configuring the Desktop uses web portal 240. Configuration primarily consists of setting up trading partners with their exchange preferences, and inbound workflow rules for receiving documents from trading partners. FIG. 3A shows a flowchart 300 for configuring the Desktop.

Configuration begins with configuring an account, which in turn begins with configuring releases. Step 310. One release is setup per partner and includes their preferred method of receiving documents (e.g., fax, Direct, etc.) and their preferred format of the content. A generic system release can also be used for incidental trading partners.

Receiving documents requires configuring Intake Download (Step 320) and configuring Intake Rules. Step 330. Configuring Intake Download involves storing settings for how received documents are exported from the system and imported into an EMR or other system for long-term storage. Intake Rules determine how to route received documents the partner's organization, and whom to notify when a new document is received based upon the To/From fax number or electronic address.

Next, the Desktop is installed. Step 340. During installation, a user is prompted for a preferred location of the managed parent directory. Now the Desktop is ready for automated syncing with the web portal. Step 350. Preferably, the Desktop will automatically sync the settings to a local managed drive. Each Release configured in the web portal will create a subfolder under the parent directory. The Desktop actively communicates with the portal to get the most recent configuration for a directory upon receipt of a new message. Any modifications made in the web portal are automatically synchronized to the Desktop.

Figure 3B:
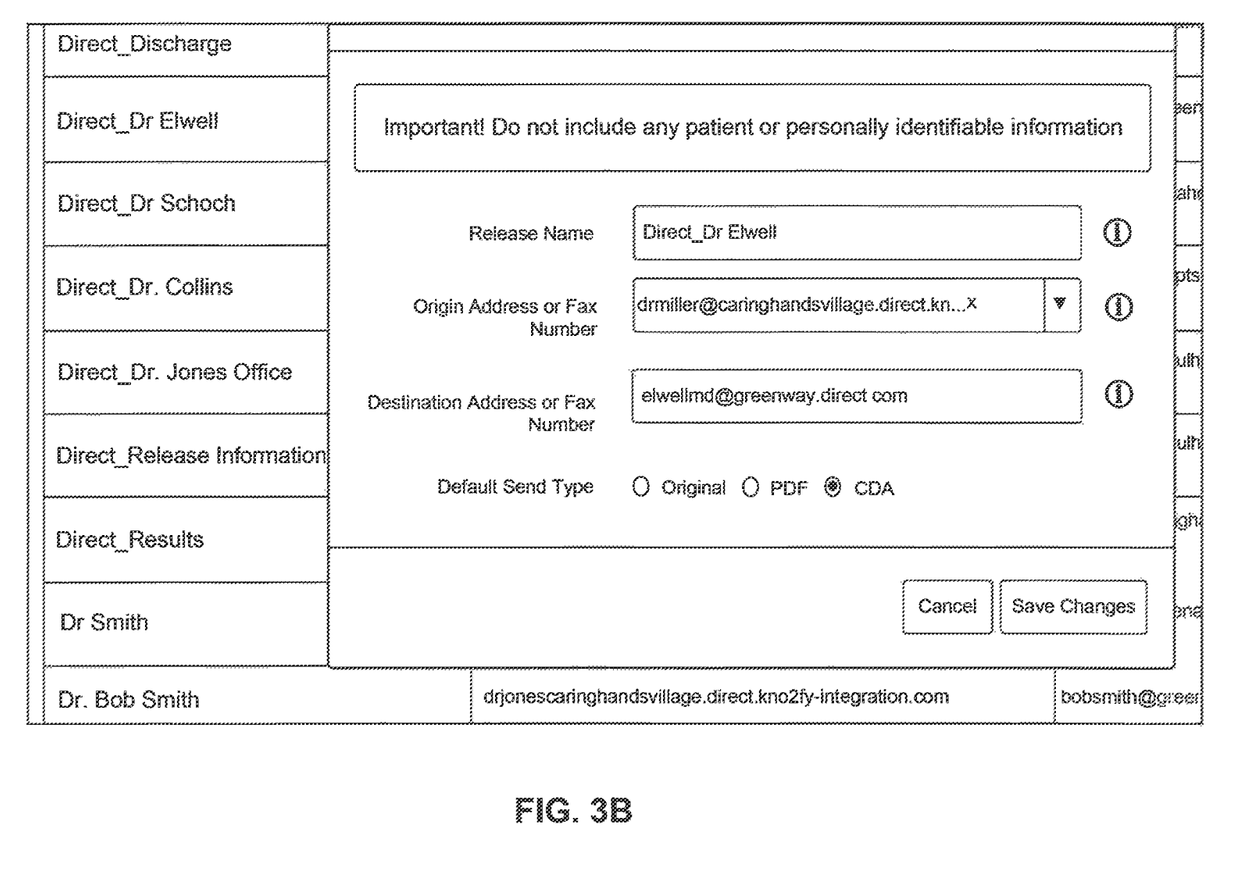
FIG. 3B is an exemplary screen shot showing a settings configuration.

FIG. 3B is an exemplary screen shot showing a settings configuration for each trading partner setup to allow for automated sending a known preference setting to ensure delivery to intended recipient/trading partner in preferred formats.

FIG. 4A is a diagram showing web release settings (on top) synchronized to local "managed" directory and subdirectories to allow for exchange from the Desktop. The releases configured in the web account automatically create folders on the Desktop for easy exchange.

FIG. 4A demonstrates the creation of "managed" folders on the desktop that becomes the point of synchronization between the desktop and the cloud and allows for efficient exchange that fits into daily workflows. The administrator would allow a Desktop user to see the folders (equivalent to Releases) that user can access. Each folder has corresponding attributes that determine which details are configured on the message when the user exports, drags and drops or virtually prints a document to one of the folders.

Figure 4B:
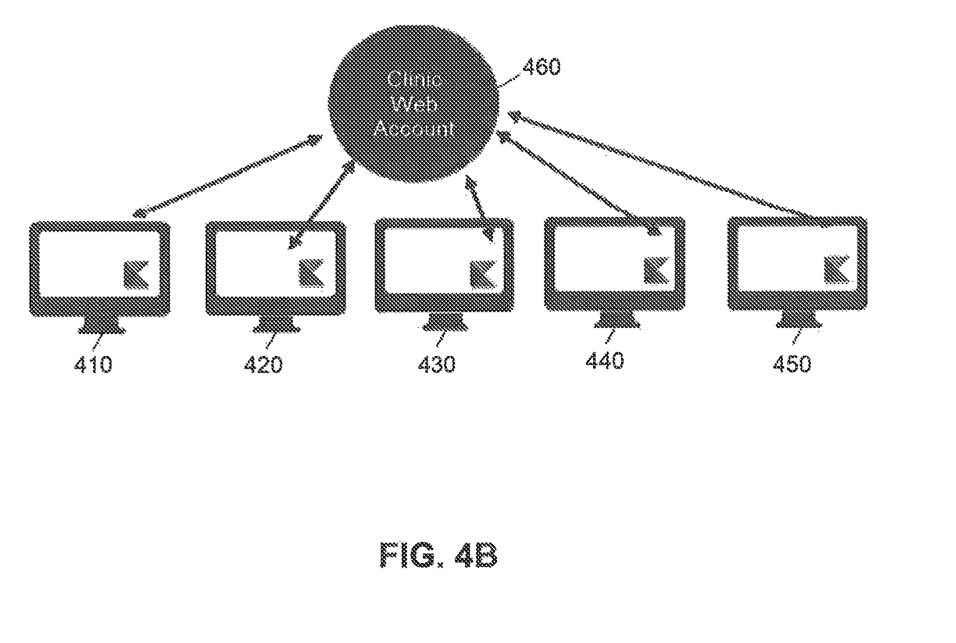
FIG. 4B is a diagram showing the relationship of Desktops to a web account.

FIG. 4B is a diagram showing various Desktops 410-50 installed and in communication with a Clinic web account 460. The web account is the original registration a healthcare organization goes through to establish its web account/portal. All users, addresses, configuration for the healthcare organization is completed within the web account.

Figure 5:
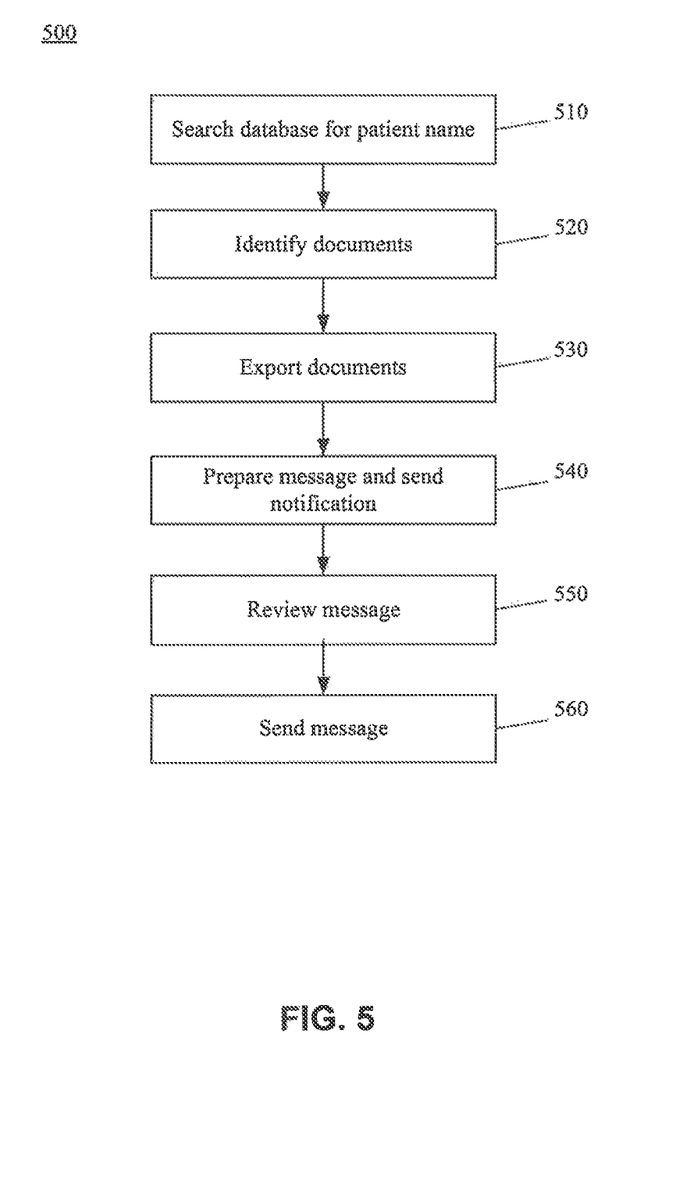
FIG. 5 shows a flowchart for sending and releasing a message via the Desktop.

FIG. 5 shows a flowchart 500 of a process for sending and releasing a message. First a user searches a database (or databases) for a patient corresponding to the message. Step 510. Next, the user identifies the document or documents to send. Step 520. The user then exports or prints the document or documents to a quick-release-type folder for the intended recipient. Step 530. The Desktop monitors the folders and, when appropriate, prepares the message and sends a notification to the user. Step 540.

When the user is ready to send the message, a click on the notification brings up a new message screen to allow the user to review the message. Step 550. For certain documents, the desktop will automatically populate fields like the patient's name, date of birth, and gender. For unstructured files, the user must enter all the information.

After reviewing the message for completeness, the user clicks on the screen to send the message. Step 560.

Figure 6:
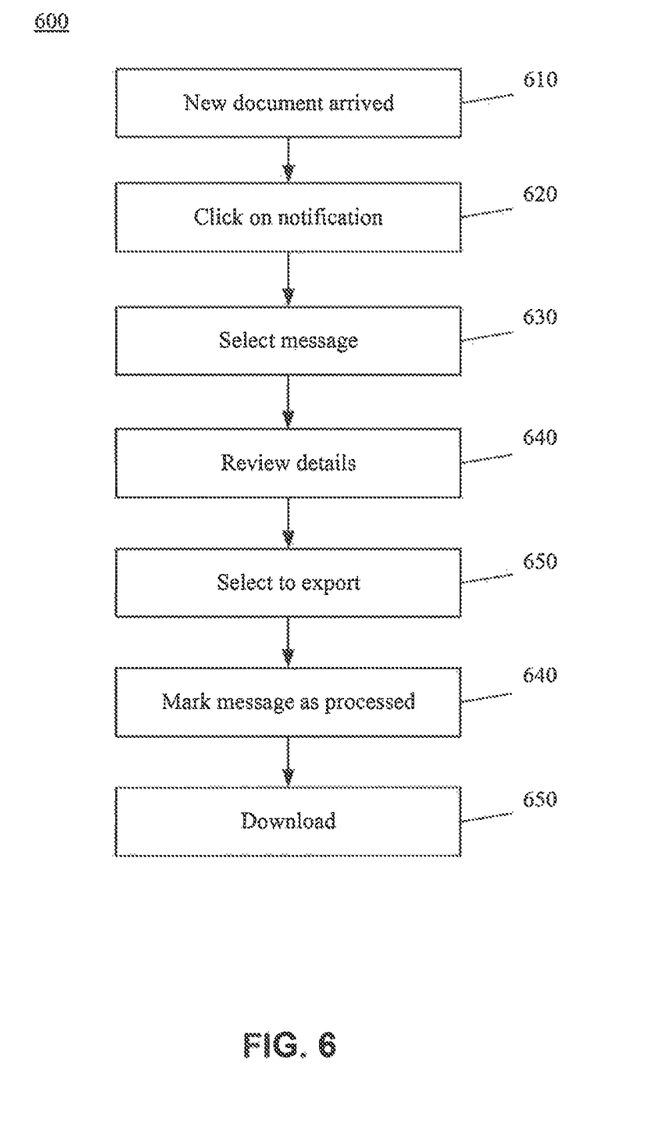
FIG. 6 shows a flowchart for receiving new patient documents via the Desktop.

FIG. 6 is a flowchart 600 for receiving new patient documents. The Desktop simplifies receiving new patient documents by avoiding the need to monitor a fax machine or server for new faxes. Instead, the Desktop immediately informs a recipient about the arrival of a new document, preferably with a pop-up notification on the desktop, and an email notification. Step 610. The user can process the message further by clicking on the notification and logging in to the Portal. Step 620.

The user then selects the message to open it (step 630), reviews the patient and attachment details for completeness (step 640), chooses whether to export the document or documents (also called attachments) (step 650), marks the message as processed (step 660), and tells the system to download. Step 670.

Figure 7:
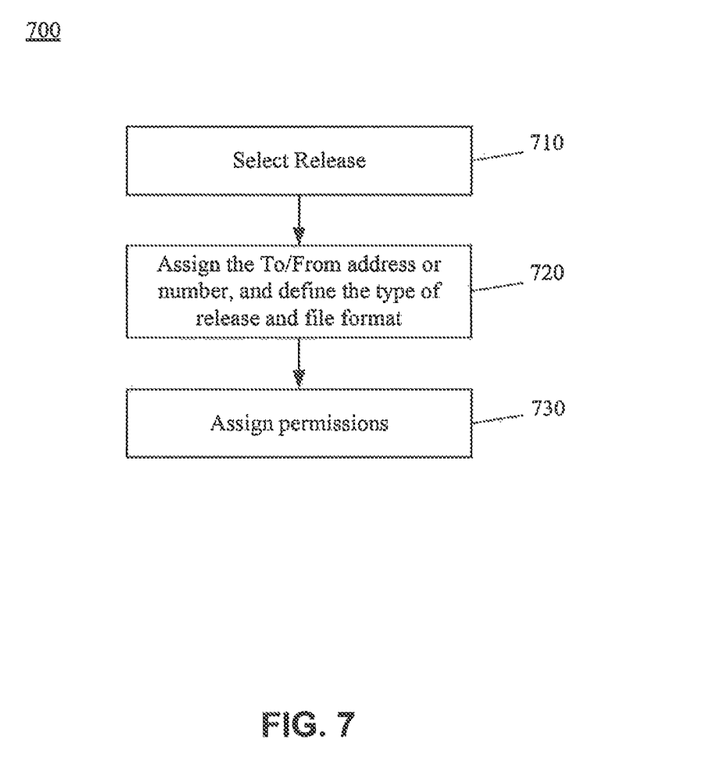
FIG. 7 shows a flowchart for setting up releases for the Desktop.

FIG. 7 shows a flowchart 700 of a process of setting up releases consistent with the invention. The first step is to select the release. Step 710. The Desktop has releases configured within the portal. Releases include a one-time setup of the providers with which a healthcare organization, for example, most often exchanges patient information.

Preferably, release is setup per common trading partner, and includes their preferred method of receiving documents (i.e.—fax, Direct, etc.) and the format of the content they would like to receive. One release is setup per trading partner. A generic or default system release may also be used for incidental trading partners.

To setup a release, an administrator assigns the To/From address or number, and defines the type of release and file format for this release. Step 720. This is the configuration of a release discussed above. The file format depends on the type of message, such as fax, Direct, or HL7.

Users are assigned permissions to the release. Step 730. Once a user is assigned permission, the Desktop automatically builds a folder on each user's computer and automatically updates the folder from the web. This folder can now be used for exporting files such as a CCD, PDF, etc., and to for initiating a new message for the address/provider on the release.

Figure 8:
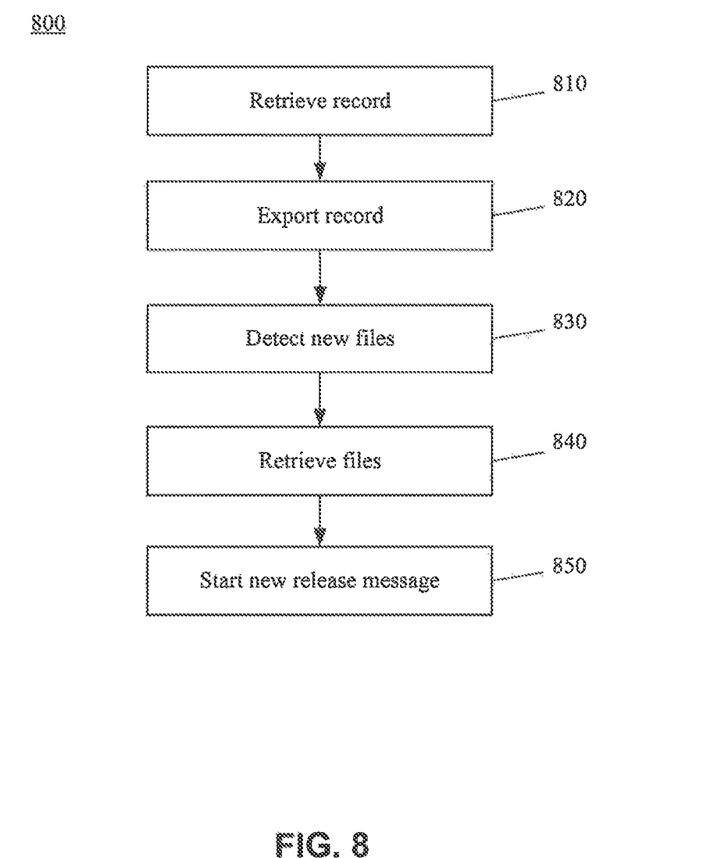
FIG. 8 shows a flowchart for sending documents using the Desktop.

When a user needs to send documents about a patient to a provider, instead of printing the documents to fax them, the user can use the Desktop. FIG. 8 shows a flowchart 800 of a process for sending documents using the Desktop consistent with the invention. First, a user retrieves the patient record or the desired portions of the record in electronic form. Step 810. Then the user activates the Desktop to export the record to the intended release folder, which corresponds to the intended recipient. Step 820. The Desktop preferably monitors all subfolders underneath a Release folder, which allows it to detect when new files are added to the corresponding subfolder (Step 830), retrieve the files (Step 840), and start a new release message. Step 850.

Preferably, files are removed from the folder and saved as draft messages to avoid unmanaged patient history information sitting on the desktop. A message pops up on the recipient's desktop with all the files attached. If a structured document, such as a CDA (clinical data architecture), is attached, the Desktop will extract patient data from the file and assign it to the message. The recipient simply reviews the message and hits "Send." In this way, the process fits seamlessly into the workflow, in the EMR or patient charts, and proceeds securely.

Figure 9:
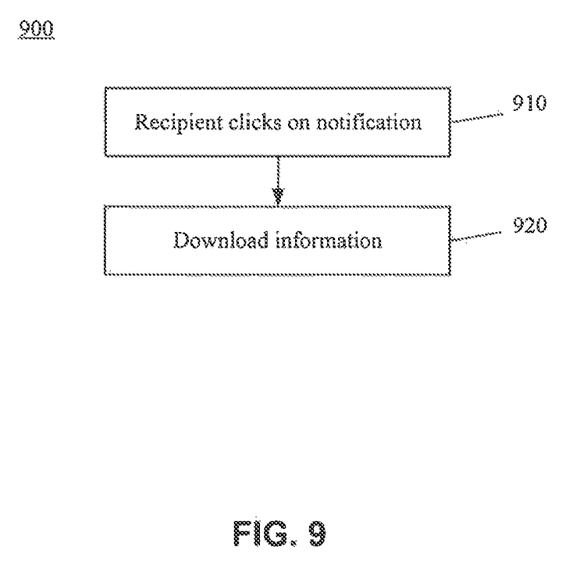
FIG. 9 shows a flowchart for receiving a message using the Desktop.

FIG. 9 is a flowchart 900 showing the process of receiving a message consistent with the invention. A recipient of a new message will receive a brief pop-up notification on the desktop, similar to receiving a notification of a new email. The recipient can click on the notification and retrieve the received message. Step 910. The recipient can then review the message and hit SAVE. This causes the information from the message to be downloaded and/or stored directly to the EMR. Step 920. This also fits into a workflow by allowing the recipient to retrieve the new message without logging into the portal.

Figure 10:
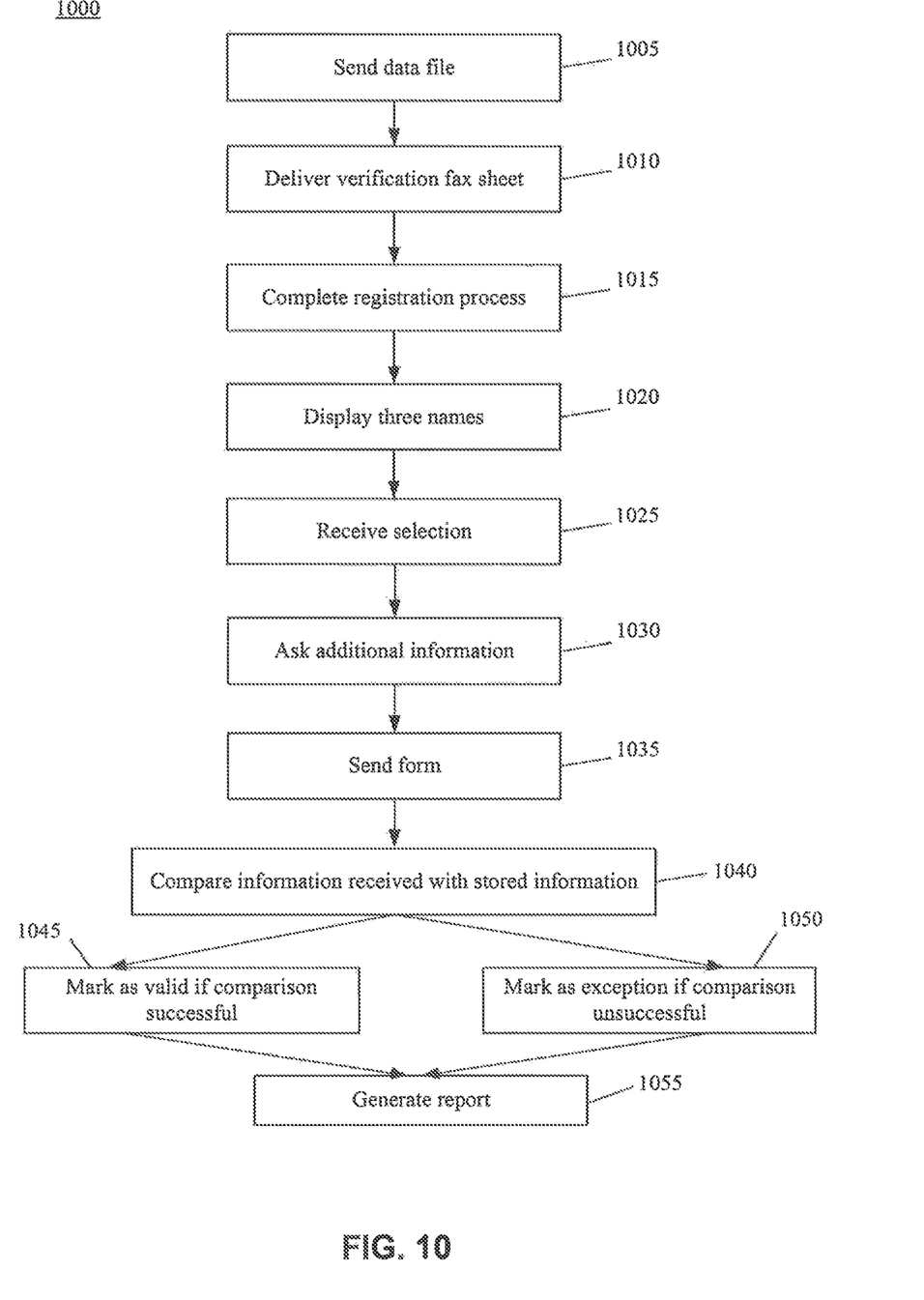
FIG. 10 shows a flowchart for verifying faxes by a healthcare system.

FIG. 10 shows a process performed by a healthcare system consistent with the preferred embodiment to verify fax numbers. The first action is to send a data file (step 1005), for example through a web-service layer, with the following information:

Provider fax number
Provider name
Provider phone number
Key demographics of a patient associated with a recent referral to the provider, the demographics possibly including combination of the following
Patient Name (first, middle, last)
Patient DOB
Patient Gender
Patient Phone(s)—Home, Work, and/or Mobile
Patient Address
Patient Email
Patient Insurance ID
Data file is uploaded to a secure website Once the data file has been uploaded, the system delivers a verification fax sheet is to the recipient explaining the process. Step 1010. The purpose of the fax sheet is to verify the validity of the fax number on file, and ensure the intended recipient still owns that number. The fax cover sheet preferably instructs the recipient to go to a browser and key in a URL specific to the transaction. The actual fax content (containing the patient information) is held and not sent until the user completes this process.

The fax sheet instructions preferably direct the recipient of the verification fax to a website to complete a short registration process to verify recipient's identity. Steps 1015.

If validation is successful, the fax recipient is then brought to a shared patient validation screen that would display three names, one being that of the actual patient. Step 1020 This security test ensures the recipient facility is familiar with the patient corresponding to the records. The recipient selects the name believed to be accurate. Step 1025. The system then asks for additional information about the selected patient as an additional check. Step 1030.

Afterwards, recipient receives a form with fields to fill in. Step 1035. Using multiple fields increases the reliability of the verification. Preferably, the fields should not be "Gender," which someone intent on fraud may guess from the name, or information that can be obtained by searching public databases using the patient's name. Instead, the fields should contain information the correct recipient should have, such as the patient's date of birth, telephone number, email address, or insurance ID.

Once the recipient has entered data into the desired fields, the system compares the information provided to matching data on file. Step 1040. If the comparison shows a sufficiently high confidence, the fax number and provider are marked as valid. Step 1045. Otherwise, the fax number is marked as an exception for manual handling. Step 1050.

Preferably, if the recipient selected the incorrect name in Step 1025, the system continues to take the recipient through the process before failing the recipient. In this way, the recipient will not know the reason for failing verification. The system may repeat the verification process if the system receives no response, or if the fax number yields no timely response.

At the end of the process, the system generates a report that includes successful, failed, and unanswered fax numbers. Step 1055.

Figure 11:
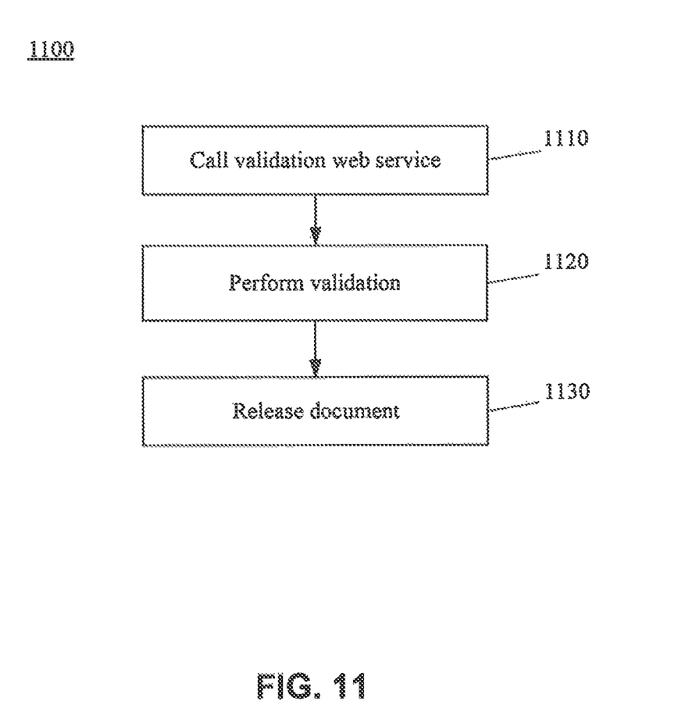
FIG. 11 shows a flowchart for providing verification of new fax numbers.

When a provider gets a new fax number, that number should be verified according to a similar process described above. FIG. 11 shows a flowchart 1100 for providing that verification. The process begins with a call to the validation web service (step 1110) so the recipient uploads the data set as described in flowchart 1000.

The system performs the validation process described above for the new number. Step 1120 Upon successful validation, the system posts an event to the fax server to release the original document. Step 1130.

Manufacturers of the fax machines, developers or apps on the machines, or developers of fax machine drivers can integrate the validation service. Upon submitting a fax to a new fax number, the machine or fax client would request the sender to input key patient demographics, which would pass to the validation service. That service would validate the new number. Upon a successful validation, the system should post an event to release the original document.

Fax numbers can be added manually into an address book. The first use of a fax number flags it as new. For new numbers, the system calls the validation web service to perform validation, Successful validation, causes the system to post an event to release the original document.

Other embodiments of the invention will be apparent to those skilled in the art from consideration of the specification and practice of the invention disclosed. The specification and examples are only exemplary, with the true scope and spirit of the invention being indicated by the following claims.

What is claimed is:

1. In a system for exchanging information via a web portal, a method for communicating from an account for a desktop application comprising the steps of:
configuring a release for a trading partner by a central data processing facility, including storing a preferred method of receiving documents and a preferred format for the content of such documents;
configuring an intake download by the central data processing facility by storing settings for exporting documents from the system and importing documents into the system;
configuring intake rules by the central data processing facility to determine how to route received documents;
installing a Desktop from the web portal onto a local data processing system;
receiving, while a user is in a workflow not specific to exchanging information via the web portal, an identification of a document from the user to be sent to the trading partner;

preparing the document in the release, wherein the document is formatted to a specified standardized format;

automatically synchronizing the Desktop to the web portal by actively communicating with the web portal to retrieve most recent configurations for a directory upon receipt of a new message, the synchronization including monitoring the release and preparing a first message including the document to be sent from the Desktop using the preferred method and in the specified standardized format; and sending the first message from the Desktop without requiring the user to leave the workflow.

2. The method of claim 1, further including the step of having the Desktop actively communicate with the web portal to get the most recent configuration upon receipt of a second message.

3. The method of claim 1, wherein the step of configuring a release includes the step of using a generic system release.

4. The method of claim 1, wherein the release is configured in the web portal to create a subfolder under a parent directory on the Desktop, and the Desktop actively communicates with the web portal to obtain a most recent configuration for the parent directory.

5. The method of claim 4, wherein the subfolder includes attributes that determine details configured on the first message when the user exports, drags and drops, or virtually prints the document to the subfolder.

6. The method of claim 1, wherein configuring intake rules include determining a recipient to notify based on a To/From fax number or electronic address from a received document.

7. The method of claim 1, wherein the Desktop immediately informs a recipient about the arrival of a new document.

8. The method of claim 1, wherein preparing the first message includes populating a new message screen to allow the user to review the message.

9. The method of claim 1, further including automatically populating certain fields in the first message based on data from the document.

10. The method of claim 1, wherein configuring the release further includes assigning a To/From address or number for the trading partner and assigning permissions to the release.

11. The method of claim 1, wherein the document is sent to a quick-release-type folder for an intended recipient.

12. The method of claim 1, wherein the file format depends on a type of message.

13. The method of claim 1, wherein the preferred method of receiving documents includes one of fax or Direct.

14. The method of claim 1, wherein the system is configured to display a pop-up notification for a received message that notifies a recipient of the received message without requiring the recipient to log into the web portal.

* * * * *